United States Patent [19]

Maselli et al.

[11] 4,321,324

[45] Mar. 23, 1982

[54] PROCESS FOR MAKING GLUCOSONE

[75] Inventors: John A. Maselli, Wilton; Robert O. Horwath, Westport, both of Conn.

[73] Assignee: Standard Brands Incorporated, New York, N.Y.

[21] Appl. No.: 160,763

[22] Filed: Jun. 18, 1980

[51] Int. Cl.³ .................. C12P 7/26; C12P 17/02; C12P 19/02
[52] U.S. Cl. .................. 435/105; 435/123; 435/148; 435/182; 435/190; 435/813; 435/819
[58] Field of Search .............. 435/105, 148, 123, 190, 435/147, 813, 819, 182, 155, 157, 158

[56] References Cited

U.S. PATENT DOCUMENTS

| 3,911,140 | 10/1975 | Osborne et al. | 435/813 X |
| 4,102,742 | 7/1978 | Klose et al. | 435/813 X |
| 4,246,347 | 1/1981 | Neidleman et al. | 435/105 |
| 4,247,641 | 1/1981 | Neidleman et al. | 435/157 X |

FOREIGN PATENT DOCUMENTS 7176 1/1980 European Pat. Off. .

OTHER PUBLICATIONS

Milas et al., *JACS*, 58, 1302–1304, (1936).
Milas et al., *JACS*, 59, 2345–2347, (1937).
Milas et al., *JACS*, 59, 543–544, (1937).
Milas, *JACS*, 59, 2342–2344, (1937).

*Primary Examiner*—Esther M. Kepplinger
*Attorney, Agent, or Firm*—Richard Kornutik

[57] ABSTRACT

Disclosed are methods of producing glucosone which comprises enzymatically oxidizing glucose with glucose-2-oxidase in a first zone and separating the concomitantly produced hydrogen peroxide from said first zone through a semi-permeable membrane into a second zone wherein an alkene is reacted with said hydrogen peroxide to form oxygenated products of said alkene, said membrane being permeable only to compounds of a molecular weight of less than about 100.

8 Claims, No Drawings

PROCESS FOR MAKING GLUCOSONE

BACKGROUND OF THE INVENTION

This invention is concerned with a new and useful process for the production of glucosone and more particularly for the production of glucosone from which food-grade fructose can be obtained.

Commercial methods for the production of fructose, a commercially important sweetner, primarily involve a two-step process, the first, hydrolysis of a polysaccharide such as starch to produce glucose and the second, isomerization of the so-produced glucose to form fructose. The latter step, as is well-known, produces a mixture of glucose and fructose from which it is difficult to separate the desired product, fructose. The commercial separation method involves the use of crystallization and/or fractionation techniques which are costly and time-consuming. More detailed description of the various methods of isomerizing glucose can be found in the literature, e.g. U.S. Pat. Nos. 3,788,945, and 3,616,221.

Glucose can also be converted to fructose by the action of an enzyme, designated glucose-2-oxidase, to form glucosone (D-arabino-2-hexosulose) which in turn can be reduced to fructose with zinc and acetic acid [Folia Micriobiol. 23, 292–298 (1978) and Czechoslovakian Pat. No. 175897 to Volc et al.].

The reaction of glucose-2-oxidase with glucose to produce glucosone also yields hydrogen peroxide in equimolar amount. The use of the so-produced hydrogen peroxide in the conversion of alkenes to corresponding halohydrins and epoxides has been proposed in European Patent Application No. 7176. In the published application, the in situ formation of hydrogen peroxide is proposed by inclusion of glucose-2-oxidase and glucose in the reaction mixture which includes a halogenating enzyme and a source of inorganic halide into which the selected alkene is to be introduced. The disclosure of the European patent application further indicates that the glucosone product of the enzymatic oxidation of glucose can be converted to fructose by simple chemical hydrogenation.

However, fructose produced by the said process can be contaminated with significant amounts of by-products from both the enzymatic conversion of glucose and the alkene conversion reaction. In particular, the latter reaction produces halohydrins and alkylene oxides, e.g. ethylene oxide, which are highly toxic materials even at levels in the region of parts per million. Thus, fructose produced by such a process will require careful and costly purification to attain foodgrade purity. Further, the potential for contamination of fructose by virtue of secondary reactions during the initial processing stage is quite high due to the highly reactive products, halohydrins and alkyleneoxides, and substantial purification procedures are required to assure the high level purity required for food grade fructose.

SUMMARY OF THE INVENTION

This invention provides a method for the production of glucosone by enzymatic oxidation of glucose to glucosone in a reaction zone from which hydrogen peroxide is removed by use of a hydrogen peroxide-permeable membrane into a second reaction zone where the hydrogen peroxide is reacted with an alkene to convert the alkene to an oxidation product.

In accordance with one embodiment of the invention, the alkene is converted to a glycol by reaction with hydrogen peroxide. This reaction is catalyzed by osmium, vanadium or chromium oxide or by ultraviolet light in accordance with the procedure described J.A.C.S. 58, 1302 (1936); 59, 543, 2342, 2345 (1937), incorporated herein by reference.

In accordance with a second embodiment of the invention, the alkene is converted to a halohydrin and then to an alkylene oxide or glycol corresponding to the original alkene reactant by reaction with hydrogen peroxide, a halogenating enzyme and a halide ion source, to form the halohydrin which is then converted to an epoxide or glycol, by the methods described in European patent application No. 7176.

The membranes employed in the present process are for the purpose of establishing two separate zones and permitting migration of hydrogen peroxide from the first to the second zone. The membranes therefore should be of suitable pore size to selectively permit hydrogen peroxide migration, but to preclude passage of larger molecules in the first reaction zone. Such membranes are readily available commercially and can be defined in terms of the molecular weight of solute particles to pass through the membrane. In the present invention, membranes which permit substances of a molecular weight of less than about 100 are to be used, and preferably less than 50.

The migration or passage of hydrogen peroxide through the aforesaid membrane is accomplished through establishment of an equilibrium predicated on the relative concentrations of $H_2O_2$ on each side of the membrane. As the concentration of hydrogen peroxide in the first zone increases, the $H_2O_2$ tends to migrate to the second zone until equilibrium is reestablished. The reaction with an alkene in the second zone increases the rate of flow of hydrogen peroxide through the membrane by offsetting the equilibrium in the direction of the second zone.

Employing the present process results in considerable advantage particularly in the further processing of glucosone to fructose. The migration of hydrogen peroxide from the first reaction zone of course affects the rate of the enzymatic oxidation of glucose so that the reaction tends to be more complete and the reaction times can be shorter than normally required. Further, the first reaction zone is essentially free of contaminants that will accumulate primarily in the second reaction zone where the so produced hydrogen peroxide is reacted. The glucosone solution produced in the first reaction zone can be filtered or used as such in the hydrogenation step or can be concentrated or otherwise processed as desired. The glucosone solution is substantially free of contaminants other than some unreacted glucose, or glucose dimer or timer, and whatever other saccharides that may have been introduced in the original glucose charge. Usually, the glucose charge will be a hydrolysate of a natural product containing glucose units, most commonly starch, which will contain soluble saccharides such as maltose, formed in the starch hydrolysis.

Accordingly, the reduction of the reaction product of the first zone will provide a product, fructose, which will be comparatively free of contaminants that affect food grade status for the product, the contaminants being derived only from the glucose natural sources, e.g. starches such as corn starch.

The alkene reaction zone also is cleaner than attainable when both reactions are conducted in the same reactor.

PREFERRED EMBODIMENTS

The membranes to be used in the present process are any of those commonly employed in aqueous systems and include a wide variety. Most commonly, the membranes will be comprised of nylon, a styrene polymer, usually polystyrene, teflon, or a cellulose ester such as cellulose acetate or propionate. In a first embodiment, the membrane is fitted into a reactor to provide two zones in a manner to preclude unintended mixing of the contents of the two zones. In a second embodiment, separate reactors can be coupled with the selected membrane providing the requisite interface in the coupling. For maximum migration of hydrogen peroxide from the first zone to the second zone, membranes of significant exposed surface area are of course preferred for which reason the first embodiment is more preferable.

The glucose-2-oxidase enzyme can be provided in the form of the enzyme solution in water, immobilized enzyme or immobilized cells or mycelium or the free cells or mycelium. Most commonly since the enzyme is intracellular, the cells or mycelia of the selected microorganism are used by merely suspending them in the reaction solution. Promoters and protectors for the enzyme can also be present. For example, as described in the aforesaid Folia Microbiol. 23, 292–298 (1978), the presence of fluoride ion promotes the enzymatic oxidation of glucose with *O. mucida*. Protectors for enzymes can also be used, e.g. Co, Mn and Mg salts.

The enzymatic oxidation reaction is carried out until substantially complete as can be determined by monitoring the mixture using aliquots to test for glucose content, or by colorimetric determination of glucosone or by determination of hydrogen peroxide. Usually, reaction periods of about 24–48 hours are sufficient, depending on enzyme potency or activity.

A wide variety of microorganisms can be used to produce the glucose-2-oxidase employed in the present process. For example, the following organisms are described in the literature for this purpose:

I. *Aspergillus parasiticus* [Biochem J. 31, 1033 (1937)]
II. *Iridophycus flaccidum* [Science 124, 171 (1956)]
III. *Oudemansiella mucida* [Folia Microbiol, 13, 334 (1968) ibid. 23, 292–298 (1978)]
IV. *Gluconobacter roseus* [J. Gen Appl. Microbiol. 1,152 (1955)]
V. *Polyporus obtusus* [Biochem. Biophys. Acta 167, 501 (1968)]
VI. *Corticium caeruleum* [Phytochemistry 1977 Vol. 16, p. 1895-7]

The temperature for the enzymatic oxidation reaction is not critical. The reaction can be conducted at room temperature, or even somewhat higher than room temperature where the enzyme system employed is of reasonable heat stability. In particular, it is preferable to operate at 50° C. and above with heat stable enzyme systems in which range bacterial infection of the reaction mixture is minimized. Alternatively, the enzymatic reaction mixture can contain antibacterial agents to preclude extensive bacterial growth.

The first reaction zone of course should contain no significant amounts of a reducing agent for hydrogen peroxide so that the beneficial results of the present process can be realised. Thus, the system should be substantially free of reducing agents for $H_2O_2$, i.e. a non reducing system.

During the course of the present process, it is possible for some diffusion of material from the second reaction zone into the first zone, especially where anions, cations or low molecular weight compounds are present in the second zone, but such diffusion is not significant under the present conditions.

The procedures employed for the conversion of alkenes to oxygenated products are those listed in the hereinbefore described references which are incorporated herein by reference for the said disclosure.

The reduction of glucosone to fructose is accomplished by known procedures including chemical reduction as with zinc and acetic acid as well as catalytic hydrogenation, with the usual metal catalysts. Of these, the preferred metal catalyst is Raney Ni since its use is compatible with the desired food grade of fructose, i.e. no residues or contaminants are left by this catalyst.

In the usual procedure employed, the glucosone is hydrogenated at elevated pressure and temperature over the selected metal catalyst until the desired degree of hydrogenation has been achieved. Pressures can range from 100 to 700 atmosphere and even higher while the temperature can range up to about 200° C. Preferred is 100° to 150° C. and a pressure of about 500 atmospheres.

The following example further illustrates the invention.

EXAMPLE

Mycelia of *O. mucida* are grown in accordance with Example 1 of Czechoslovakian Pat. No. 175897 and the equivalent of 15 g. (dry weight) of the mycelia are suspended in 3 L. of 2.5% glucose solution 0.05 M NaF in one zone of a 10 L. reactor fitted with a hydrogen peroxide-permeable membrane to form two zones. In the second zone, ethylene gas is bubbled through an aqueous solution of chloroperoxidase and halide ion buffered with a phosphate buffer (0.1 M potassium phospate) as described in European patent application No. 7176 (Examples 1–18).

The suspension in the first zone is mixed at 25° C. and aerated with oxygen. After 24 hours the mycelia are then separated from the solution in the first zone and resulting clear solution is then hydrogenated over Raney Ni at 500 atmospheres hydrogen gas and 100° C. The aqueous mixture is filtered clear of the catalyst, decolorized with carbon, deionized with ion-exchange (anionic and cationic) and concentrated to a fructose syrup at reduced pressure. Alternatively, the aqueous mixture is concentrated and fructose allowed to crystallize.

The fructose obtained as either syrup or crystalline product is of food grade quality.

The halohydrins obtained by the reaction in the second zone are converted to the corresponding epoxides by treatment with sodium hydroxide.

Essentially the same results are obtained when *O. mucida* is replaced with the following organisms:

*Polyporus obtusus*
*Radulum casearium*
*Lenzites trabea*
*Irpex flavus*
*Polyporus versicolor*

*Pellicularia filamentosa*
*Armillaria mellea*
*Schizophyleum commune*
*Corticium caeruleum*

What is claimed is:

1. A method of producing glucosone which comprises enzymatically oxidizing glucose with glucose-2-oxidase in a first zone to provide glucosone and hydrogen peroxide therein, separating hydrogen peroxide from said first zone through a semi-permeable membrane into a second zone while substantially retaining the glucosone in said first zone and reacting an alkene with said hydrogen peroxide in said second zone to form oxygenated products of said alkene, said membrane being permeable only to compounds of a molecular weight of less than about 100.

2. The method according to claim 1 wherein the product of said reaction of an alkene with hydrogen peroxide is a glycol.

3. The method according to claim 1 wherein the product of said reaction of an alkene with hydrogen peroxide is the corresponding alkylene halohydrine.

4. The method according to claim 1 where said membrane is permeable only to compounds of a molecular weight of less than about 50.

5. A method of producing fructose which comprises the steps of
    (a) producing glucosone which comprises enzymatically oxidizing glucose with glucose-2-oxidase in a first zone to provide glucosone and hydrogen peroxide therein, separating hydrogen peroxide from said first zone through a semi-permeable membrane into a second zone while substantially retaining the glucosone in said first zone and reacting an alkene with said hydrogen peroxide in said second zone to form oxygenated products of said alkene, said membrane being permeable only to compounds of a molecular weight of less than about 100, and
    (b) reducing the so-produced glucosone to obtain fructose.

6. The method according to claim 5 wherein the reduction is effected by catalytic hydrogenation.

7. The method according to claim 6 wherein the catalyst is Raney Ni.

8. The method according to claim 5 wherein the reaction mixture obtained in Step a is filtered and the filtered reaction mixture is employed in step b.

* * * * *